United States Patent
Meltzer et al.

[11] Patent Number: 5,915,284
[45] Date of Patent: Jun. 22, 1999

[54] MULTIPLE CHANNEL PIPETTING DEVICE

[75] Inventors: Walter C. Meltzer, New Milford; Edward J. Malvey, III, Norwalk, both of Conn.

[73] Assignee: Cyberlab, Inc., Brookfield, Conn.

[21] Appl. No.: 08/980,082

[22] Filed: Nov. 26, 1997

Related U.S. Application Data

[63] Continuation-in-part of application No. 08/686,173, Jul. 22, 1996, abandoned.

[51] Int. Cl.$^6$ .................................................. G01N 1/14
[52] U.S. Cl. ............................................... 73/864.17
[58] Field of Search ........................... 73/863.32, 864.16, 73/864.17, 864.14; 422/100

[56] References Cited

U.S. PATENT DOCUMENTS

| | | |
|---|---|---|
| 3,650,306 | 3/1972 | Lancaster . |
| 3,754,863 | 8/1973 | Reunanen . |
| 4,047,438 | 9/1977 | Sekine . |
| 4,158,035 | 6/1979 | Haase et al. . |
| 4,258,761 | 3/1981 | Bennett, Jr. . |
| 4,554,839 | 11/1985 | Hewett et al. . |
| 5,055,263 | 10/1991 | Meltzer . |
| 5,226,462 | 7/1993 | Carl . |

*Primary Examiner*—Robert Raevis
*Attorney, Agent, or Firm*—Hoffman, Wasson & Gitler

[57] ABSTRACT

This invention is a multiple channel pipetting device for aspirating and dispensing volumes of liquid using disposable or non-disposable tips. The device is comprised of a main body made of a hard synthetic material with multiple channels and an associated ram plate activated by a four-quadrant synchronous drive. The drive assembly is mounted on four standoffs, and the ram plate moves up and down by the means of four lead screws moved with a synchronous fibrous belt moved with a motor. A moveable plate mounted to the bottom of the device to remove disposable tips is activated by a set of automated ejector plate arms. The entire device can be mounted in a self-contained housing or attached to another device allowing it to be moved.

2 Claims, 6 Drawing Sheets

MULTIPLE CHANNEL PIPETTING DEVICE

This application is a CIP of application Ser. No. 08/686,173, filed on Jul. 22, 1996, now abandoned.

BACKGROUND OF THE INVENTION

The invention relates to a liquid pipetting device for delivery of very small quantities of liquid in a multiple well format with a high degree of repeatability and accuracy. Pipetting operations have many and varied applications in medicine and industry. For example, pipetting operations are used in various medical and chemical testing and analyzing procedures where the ability to pipette accurately with a device which has multiple channels would be highly beneficial. If this device could be lightweight and be mounted to a device such as described in the co-assigned U.S. Pat. Nos. 5,055,263 and 5,3067,510 entitled AUTOMATED PIPETTING SYSTEM (hereinafter the "Meltzer Robot"), the benefit would be even more apparent.

The multiple channel pipetting device of this invention has as one of its objects to pipette varying volumes of liquid into multiple wells and, if using disposable pipette tips, to automatically eject those tips when desired by the user. If all the tips fail to eject a signal will be emitted by a sensor, such as an optical interrupt switch, triggering an alarm, such as a warning message displayed on a computer screen, that all the tips have not been ejected by the multiple channel pipetting device.

Current state of the art pipetting devices frequently use long tubing and many fittings which malfunction and are hard to change. For example, leaky connections, defective tubing, and stripped fittings may all cause malfunctioning. Long tubing lengths can adversely affect the accuracy of pipetting.

SUMMARY OF THE INVENTION

The principal object of the invention is to provide a device which is particularly designed for pipetting small volumes of liquid into multiple wells at the same time.

With one state-of-the-art multiple pipetting device, the pipetting is done using syringes connected to multiple channels with lengths of tubing. Such a known technique has the drawback that the air inside the tubing causes inaccuracies in the pipetting of small volumes of liquids. Another state-of-the-art multiple pipetting device uses separate glass syringes which are mounted together onto a moveable plate which when activated causes the device to aspirate or dispense. Such a known technique has the drawback that it cannot easily use disposable pipette tips. Both state-of-the-art devices mentioned above, because of their weight and size, are essentially non-moveable by a device such as the Meltzer Robot.

The multiple channel pipetting device of this invention provides a simple, lightweight method for pipetting small volumes of liquid into multiple wells at the same time using either fixed probes, disposable pipette tips or a molded tip array. The accuracy of the device is <1% at 100 ul.

A small motor moves a ram plate with multiple pistons in and out of a multiple channel main body allowing the device to aspirate and dispense. The device uses the same motor to pipette liquids as to eject the disposable tips or molded tip array. The use of the same motor for both actions has the advantage of being lightweight with a reduced cost to manufacture and greater reliability. The nozzles which pick up the disposable tips or molded tip arrays are part of the multiple channel main body, so there is no need for tubing. If the fixed probes are used, they are also part of the multiple chamber main body and consequently there is no need for tubing. If the fixed probes are used, they are also part of the multiple chamber main body and consequently there is no need for tubing. This direct connection between the nozzles or fixed probes and the multiple chamber body has the advantage of greater accuracy in pipetting, lighter weight and easy mounting onto devices like the Meltzer Robot.

Four lead screws with anti-backlash nuts are activated by a belt mounted onto the device and controlled by a single motor with a series of sprockets, idlers and tension bars used to control the motion of the device.

BRIEF DESCRIPTION OF THE DRAWINGS

With these and other objects in view, which will become apparent in the following detailed description, the present invention, which is shown by example, will be clearly understood in connection with the accompanying drawings, in which.

DETAILED DESCRIPTION OF THE PREFERRED EMBODIMENT

Figure 1:
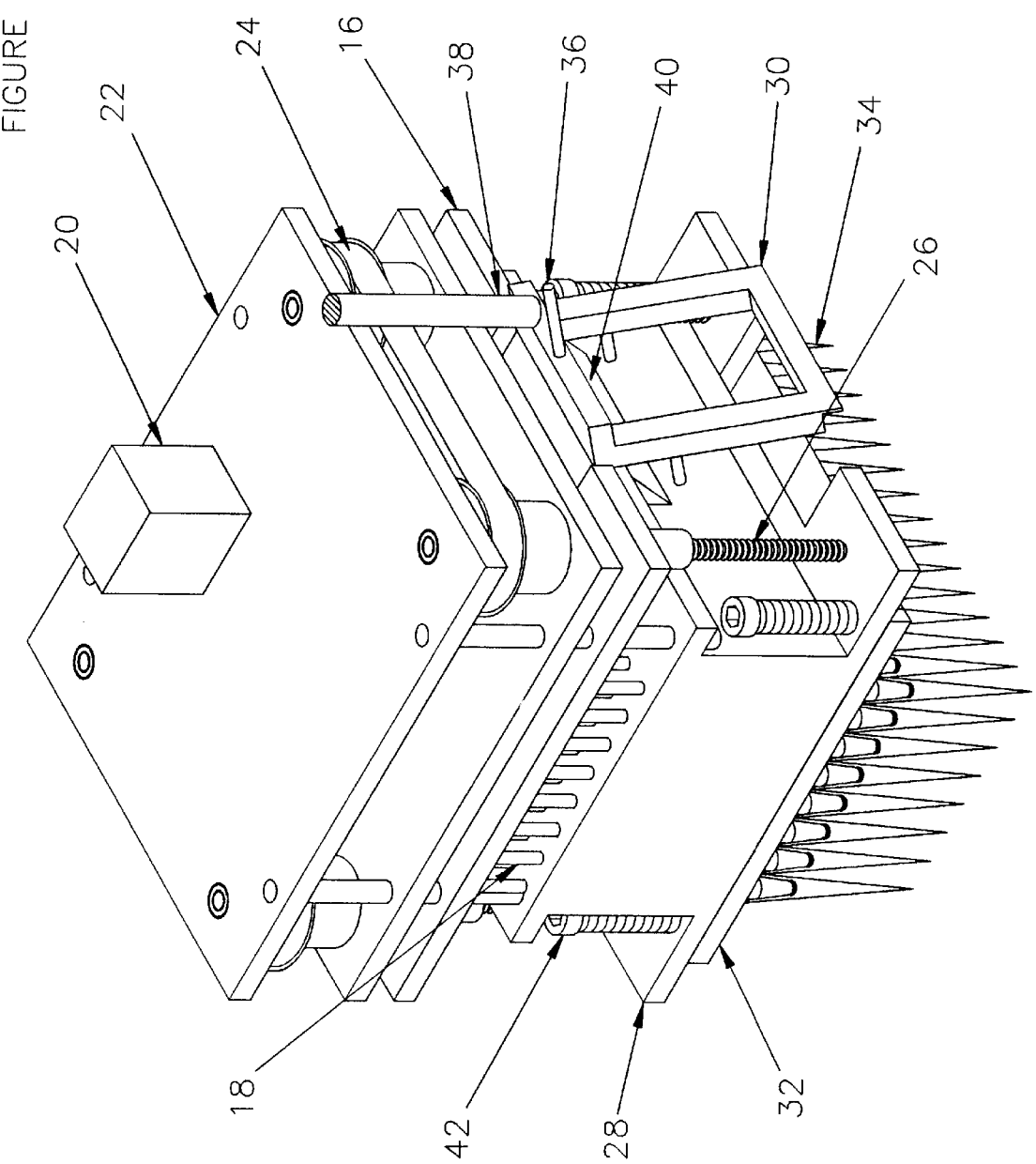
FIG. 1 is a perspective view of the multiple pipetting device in its home position.

Referring now to the Figures, there is illustrated in FIGS. 1–6 a multiple channel pipetting device embodying the present invention. The device includes a ram plate 16 on which there are mounted, preferably pressed, multiple pistons 18, usually made of stainless steel. The entire device is attached to a probe head, not shown, which allows for automated titration to occur. There is provided a motor 20 which is placed on a mounting plate 22. The motor drives a belt 24 which functions to move the ram plate 16 up and down along four screws 26 which are located at the four corners of the device. The main body 28 is preferably made of a plastic material and when the device is activated, the ram plate moves up and down by means of the four screws 26. The ram plate 16 has an ejector arm 30 which moves down engaging the ejector plate 32 causing the plate to move and knock the pipette tips 34 off the multiple pipetting device. The device depicted in FIG. 1 is in a home position. The device has already picked up a set of disposable tips 34. The ejector arm 30 is positioned away from the multiple pipetting device allowing the ram plate 16 to move freely and pipette liquids.

Figure 2:
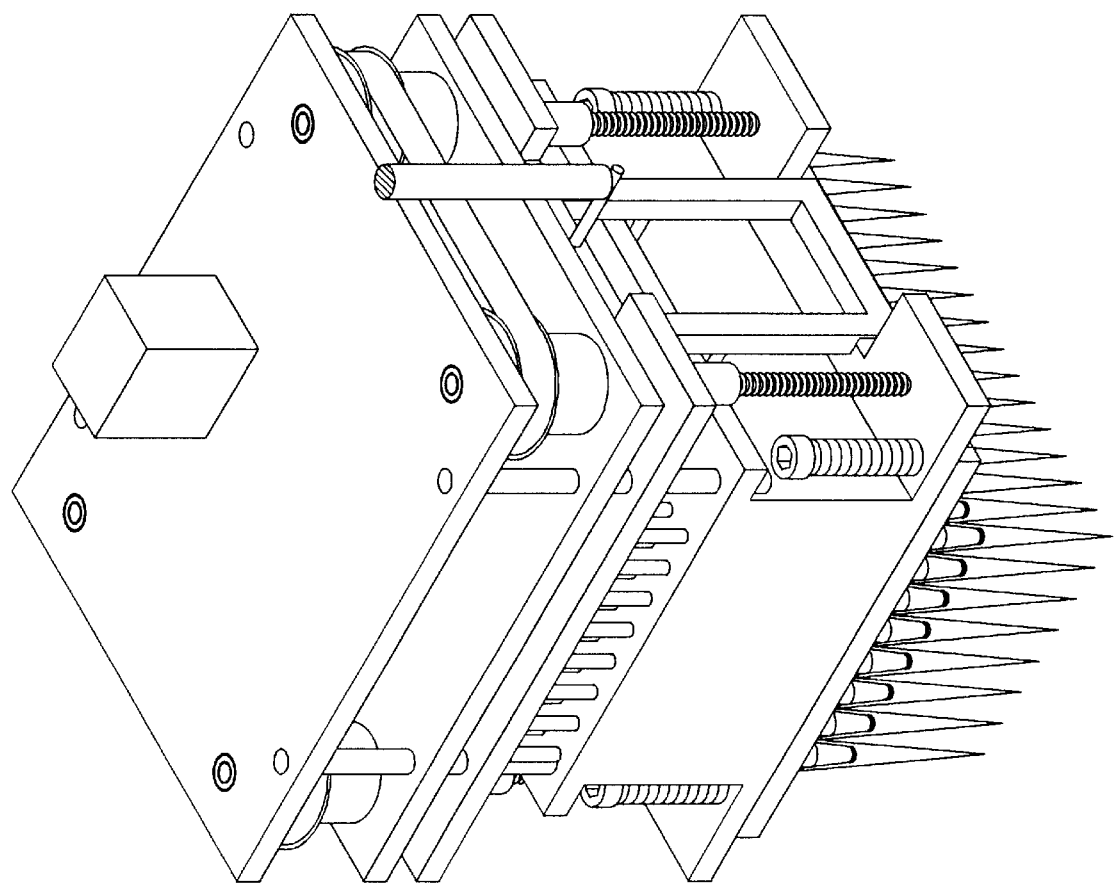
FIG. 2 is a perspective view of the multiple channel pipetting device in the arming position.

The multiple pipetting device in FIG. 2 is moved up to a negative home position forcing the ejector arm 30 down by pushing a standoff 36 connected to the ejector arm 30 with a stationary post 38 which is secured, if desired, to a probe head, not shown. The ejector arm 30 is now positioned adjacent the multiple pipetting device. In this position, the arm 30 is in a position to engage the ejector plate 32.

Figure 3:
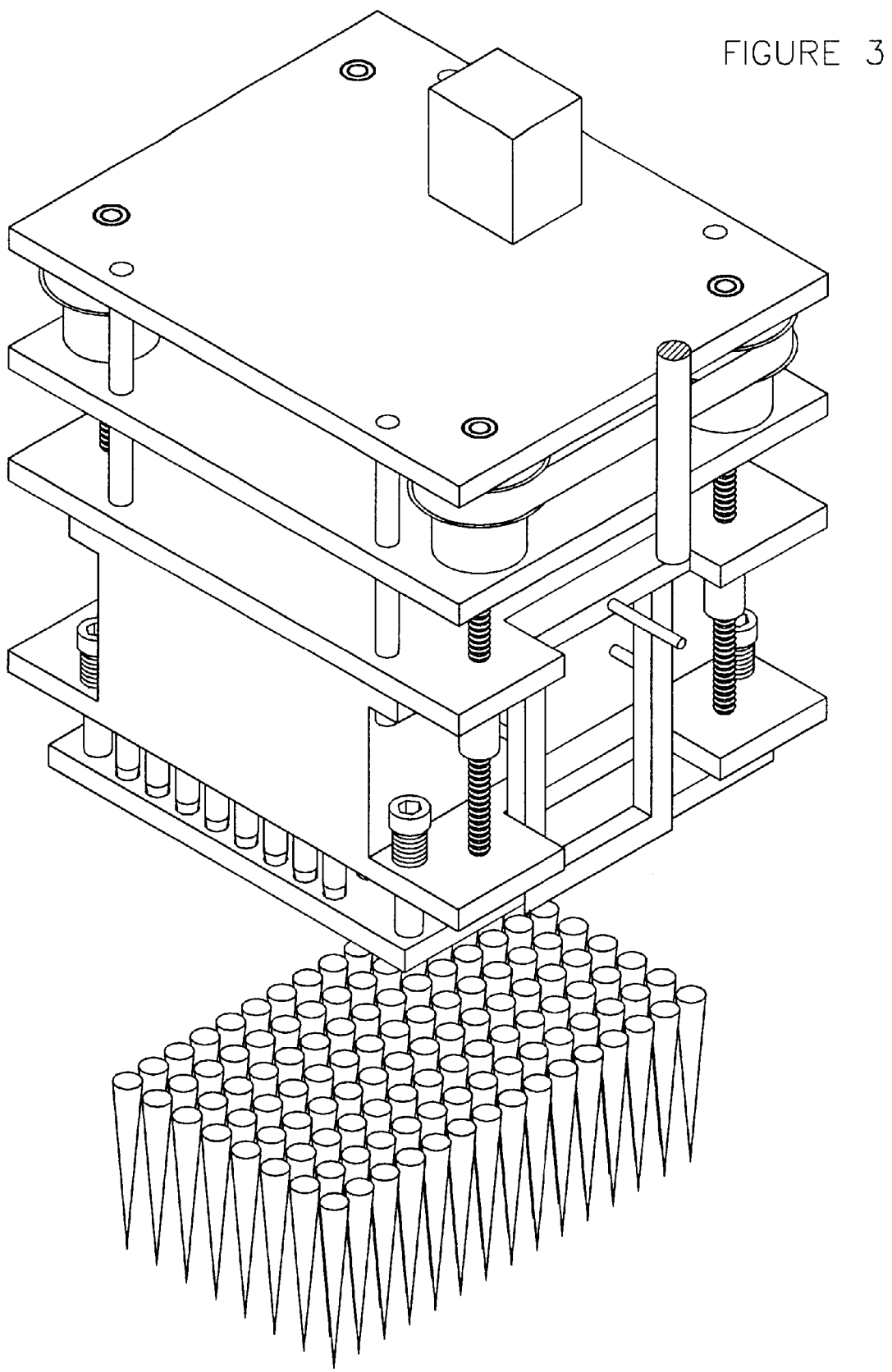
FIG. 3 is a perspective view of the multiple channel pipetting device in the ejecting position.

FIG. 3 depicts the multiple channel pipetting device in the ejecting position. The ram plate 16, with ejector arm 30 in the armed position moves down engaging the ejector plate 32 causing the ejector plate 32 to move and knock the pipetting tips 34 off the multiple pipetting device.

Figure 4:
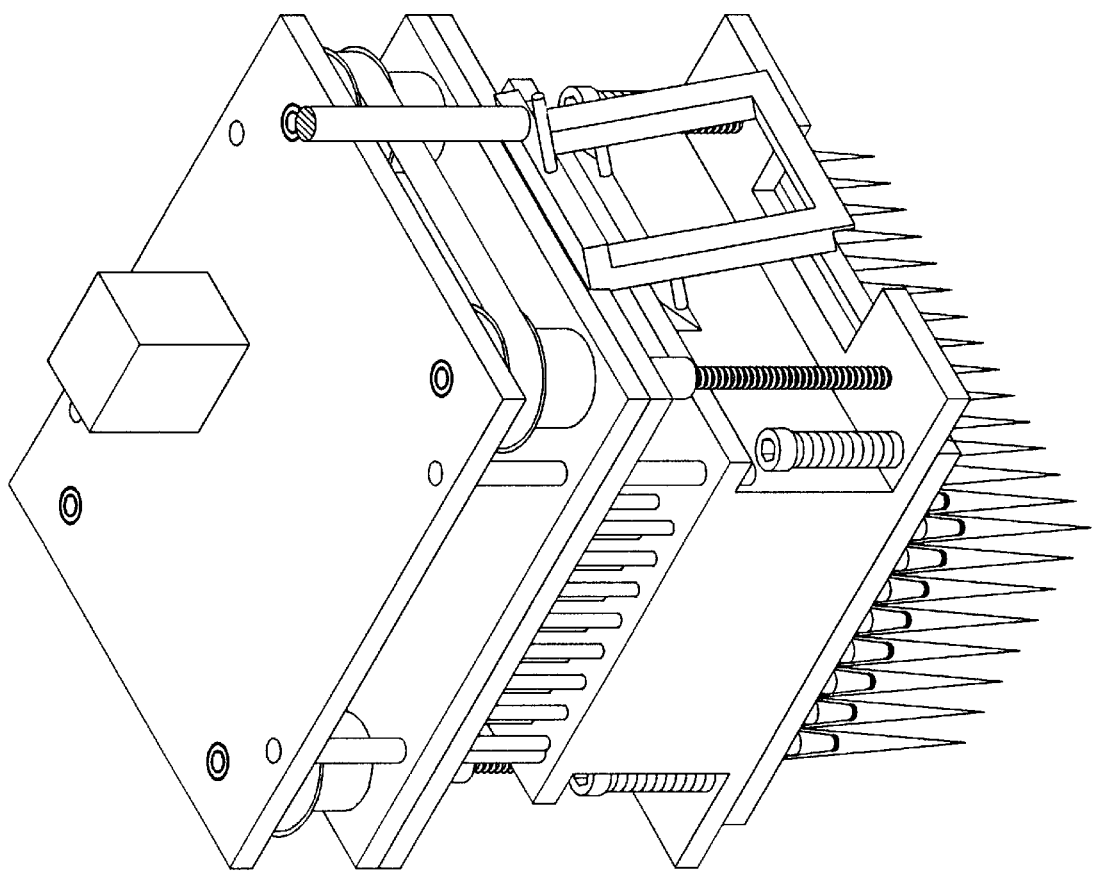
FIG. 4 is a perspective view of the multiple channel pipetting device in the disarming position.

FIG. 4 illustrates the disarming position of the device. The ram plate 16 moves up forcing the ejector arm 30 to move away from the multiple pipetting device when the stand off 36 attached to the ejector arm 30 comes in contact with a ramp 40. The multiple pipetting device is then free to pick up new pipetting tips and operate as a syringe pump.

Figure 5:
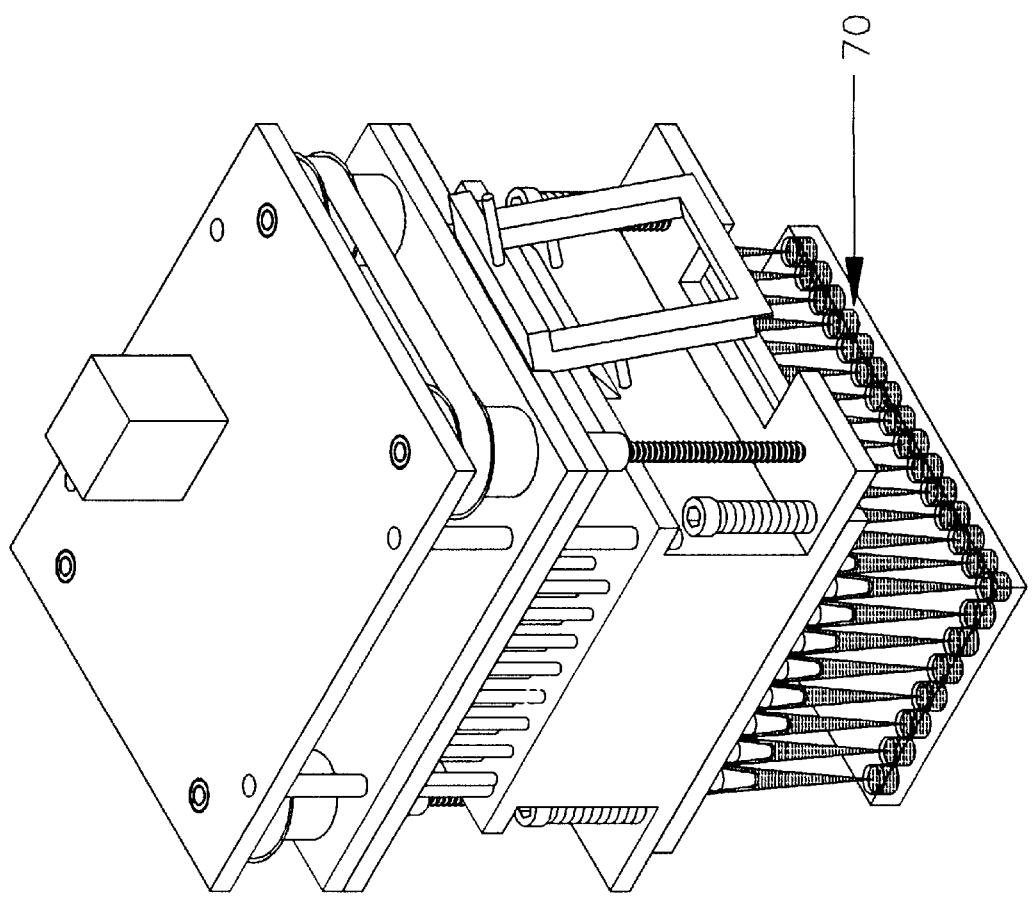
FIG. 5 is a perspective view of the multiple channel pipetting device picking up liquid from a tray.
Figure 6:
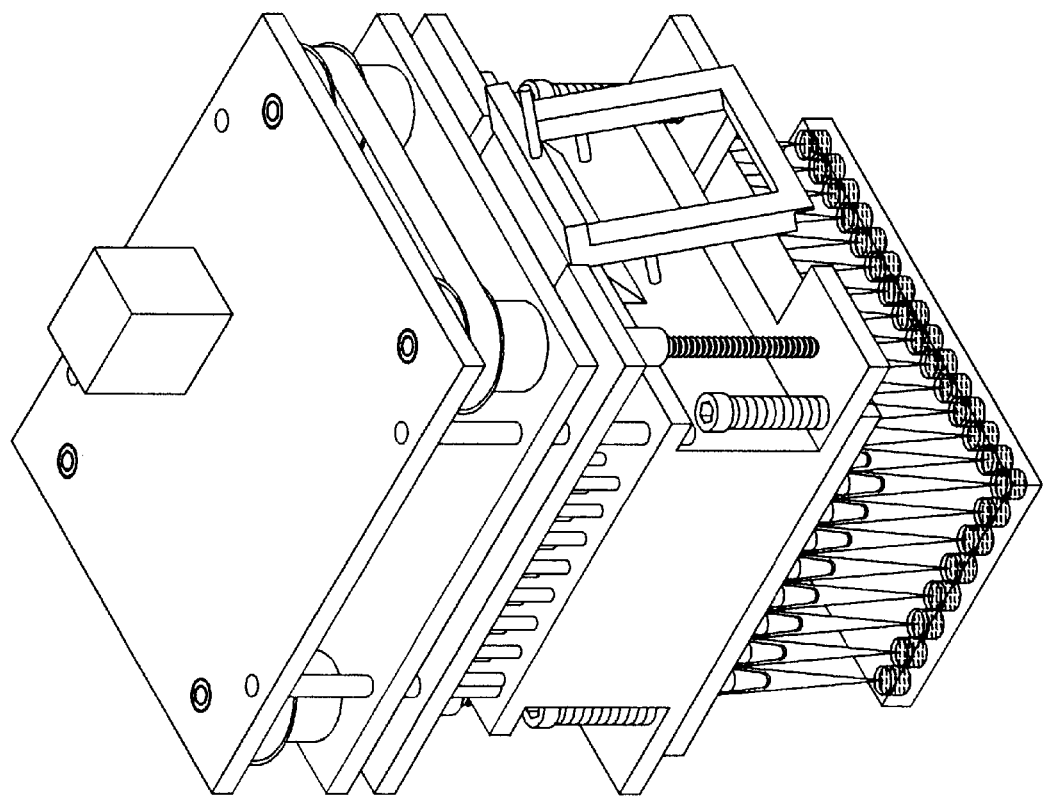
FIG. 6 is a perspective view of a multiple channel pipetting device having already picked up liquid into the pipette tip.

FIGS. 5 and 6 illustrate the multiple pipetting device picking up a liquid from a tray 70.

A plurality of springs 42 are provided to allow the ejector plate 32 to resiliently return to the home position of the device.

While the invention has been particularly shown and described with reference to a preferred embodiment thereof, it will be understood by those in the art that various changes in form and details may be made therein without departing from the spirit and scope of the invention.

What is claimed is:

1. A multiple channel pipetting device for dispensing and aspirating volumes of liquid comprising:

a main body having a plurality of holes bored therethrough;

a ram plate having a plurality of pistons mounted thereon which correspond to and engage said multiple holes;

a mounting plate attached to said ram plate, having a motor, and a drive mechanism attached thereto for driving said pistons and an ejector mechanism;

said ejector mechanism comprising:

an ejector arm attached to said ram plate which moves along a ramp and engages an ejector plate which is attached to said main body by a plurality of springs; and a stationary post which engages a stand off located on said ejector arm to move said ejector arm along said ramp for engagement on to said ejector plate; and whereby said ram plate with ejector arm moves down thereby causing said ejector plate to move and knock a plurality of pipette tips off said multiple pipetting device.

2. A process for dispensing or aspirating of liquids utilizing the device of claim 1, wherein said multiple pipetting device picks up a set of disposable tips in a home position;

said multiple pipetting device moves to a negative home position forcing said ejector arm down by pushing said stand- off connected to said ejector arm down said stationary post, said ejector arms are now positioned adjacent said multiple pipetting device to engage said ejector plate;

moving said ram plate with said ejector arm into an armed position down thereby engaging said ejector plate and causing said ejector plate to move and knock off a said plurality of pipette tips off said multiple pipetting device; and moving said ram plate up forcing said ejector arm to move away from said multiple pipetting device allowing same to return to an initial position for picking up a new set of said multiple pipette tips.

* * * * *